US011911147B1

(12) United States Patent
Berme et al.

(10) Patent No.: US 11,911,147 B1
(45) Date of Patent: Feb. 27, 2024

(54) BODY SWAY MEASUREMENT SYSTEM (71) Applicant: Bertec Corporation, Columbus, OH (US)

(72) Inventors: Necip Berme, Worthington, OH (US); Murat Kerim Berme, Venice, CA (US); Fernando Vanderlinde dos Santos, Columbus, OH (US); Mohan Chandra Baro, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 17/836,935

(22) Filed: Jun. 9, 2022

Related U.S. Application Data (63) Continuation-in-part of application No. 17/141,014, filed on Jan. 4, 2021, now abandoned.

(60) Provisional application No. 62/957,178, filed on Jan. 4, 2020.

(51) Int. Cl.
*A61B 5/11* (2006.01)
*A61B 5/00* (2006.01)

(52) U.S. Cl.
CPC .......... *A61B 5/1113* (2013.01); *A61B 5/0002* (2013.01); *A61B 5/0077* (2013.01); *A61B 5/1128* (2013.01); *A61B 5/6803* (2013.01); *A61B 5/681* (2013.01); *A61B 5/6898* (2013.01); *A61B 5/7264* (2013.01); *A61B 5/7275* (2013.01); *A61B 5/742* (2013.01); *A61B 2562/0219* (2013.01)

(58) Field of Classification Search
CPC ... A61B 5/1113; A61B 5/0002; A61B 5/0077; A61B 5/1128; A61B 5/6803; A61B 5/681; A61B 5/6898; A61B 5/7264; A61B 5/7275; A61B 5/742
See application file for complete search history.

(56) References Cited

U.S. PATENT DOCUMENTS

| | | | |
|---|---|---|---|
| 6,038,488 | A | 3/2000 | Barnes et al. |
| 6,113,237 | A | 9/2000 | Ober et al. |
| 6,152,564 | A | 11/2000 | Ober et al. |
| 6,295,878 | B1 | 10/2001 | Berme |

(Continued)

OTHER PUBLICATIONS

First office action on the merits (Non-Final Rejection) in U.S. Appl. No. 17/141,014, dated Mar. 4, 2021.

(Continued)

*Primary Examiner* — Daniel L Cerioni
(74) *Attorney, Agent, or Firm* — The Law Office of Patrick F. O'Reilly III, LLC (57) ABSTRACT A body sway measurement system is disclosed herein. The body sway measurement system includes an inertial measurement unit or camera configured to generate time series output data for determining one or more parameters indicative of the body sway of a user; and a mobile device or other computing device having a data processor, the data processor including at least one hardware component, the data processor being operatively coupled to the inertial measurement unit or camera, the data processor configured to receive the time series output data from the inertial measurement unit or camera, and the data processor and/or a cloud server configured to determine the one or more parameters indicative of the body sway of the user using a trained neural network.

20 Claims, 5 Drawing Sheets

(56) References Cited

U.S. PATENT DOCUMENTS

| | | |
|---|---|---|
| 6,354,155 B1 | 3/2002 | Berme |
| 6,389,883 B1 | 5/2002 | Berme et al. |
| 6,936,016 B2 | 8/2005 | Berme et al. |
| 8,181,541 B2 | 5/2012 | Berme |
| 8,315,822 B2 | 11/2012 | Berme et al. |
| 8,315,823 B2 | 11/2012 | Berme et al. |
| D689,388 S | 9/2013 | Berme |
| D689,389 S | 9/2013 | Berme |
| 8,543,540 B1 | 9/2013 | Wilson et al. |
| 8,544,347 B1 | 10/2013 | Berme |
| 8,643,669 B1 | 2/2014 | Wilson et al. |
| 8,700,569 B1 | 4/2014 | Wilson et al. |
| 8,704,855 B1 | 4/2014 | Berme et al. |
| 8,764,532 B1 | 7/2014 | Berme |
| 8,847,989 B1 | 9/2014 | Berme et al. |
| D715,669 S | 10/2014 | Berme |
| 8,902,249 B1 | 12/2014 | Wilson et al. |
| 8,915,149 B1 | 12/2014 | Berme |
| 9,032,817 B2 | 5/2015 | Berme et al. |
| 9,043,278 B1 | 5/2015 | Wilson et al. |
| 9,066,667 B1 | 6/2015 | Berme et al. |
| 9,081,436 B1 | 7/2015 | Berme et al. |
| 9,168,420 B1 | 10/2015 | Berme et al. |
| 9,173,596 B1 | 11/2015 | Berme et al. |
| 9,200,897 B1 | 12/2015 | Wilson et al. |
| 9,277,857 B1 | 3/2016 | Berme et al. |
| D755,067 S | 5/2016 | Berme et al. |
| 9,404,823 B1 | 8/2016 | Berme et al. |
| 9,414,784 B1 | 8/2016 | Berme et al. |
| 9,468,370 B1 | 10/2016 | Shearer |
| 9,517,008 B1 | 12/2016 | Berme et al. |
| 9,526,443 B1 | 12/2016 | Berme et al. |
| 9,526,451 B1 | 12/2016 | Berme |
| 9,558,399 B1 | 1/2017 | Jeka et al. |
| 9,568,382 B1 | 2/2017 | Berme et al. |
| 9,622,686 B1 | 4/2017 | Berme et al. |
| 9,763,604 B1 | 9/2017 | Berme et al. |
| 9,770,203 B1 | 9/2017 | Berme et al. |
| 9,778,119 B2 | 10/2017 | Berme et al. |
| 9,814,430 B1 | 11/2017 | Berme et al. |
| 9,829,311 B1 | 11/2017 | Wilson et al. |
| 9,854,997 B1 | 1/2018 | Berme et al. |
| 9,916,011 B1 | 3/2018 | Berme et al. |
| 9,927,312 B1 | 3/2018 | Berme et al. |
| 10,010,248 B1 | 7/2018 | Shearer |
| 10,010,286 B1 | 7/2018 | Berme et al. |
| 10,085,676 B1 | 10/2018 | Berme et al. |
| 10,117,602 B1 | 11/2018 | Berme et al. |
| 10,126,186 B2 | 11/2018 | Berme et al. |
| 10,216,262 B1 | 2/2019 | Berme et al. |
| 10,231,662 B1 | 3/2019 | Berme et al. |
| 10,264,964 B1 | 4/2019 | Berme et al. |
| 10,331,324 B1 | 6/2019 | Wilson et al. |
| 10,342,473 B1 | 7/2019 | Berme et al. |
| 10,390,736 B1 | 8/2019 | Berme et al. |
| 10,413,230 B1 | 9/2019 | Berme et al. |
| 10,463,250 B1 | 11/2019 | Berme et al. |
| 10,527,508 B2 | 1/2020 | Berme et al. |
| 10,555,688 B1 | 2/2020 | Berme et al. |
| 10,646,153 B1 | 5/2020 | Berme et al. |
| 10,722,114 B1 | 7/2020 | Berme et al. |
| 10,736,545 B1 | 8/2020 | Berme et al. |
| 10,765,936 B2 | 9/2020 | Berme et al. |
| 10,803,990 B1 | 10/2020 | Wilson et al. |
| 10,853,970 B1 | 12/2020 | Akbas et al. |
| 10,856,796 B1 | 12/2020 | Berme et al. |
| 10,860,843 B1 | 12/2020 | Berme et al. |
| 10,945,599 B1 | 3/2021 | Berme et al. |
| 10,966,606 B1 | 4/2021 | Berme |
| 11,033,453 B1 | 6/2021 | Berme et al. |
| 11,052,288 B1 | 7/2021 | Berme et al. |
| 11,054,325 B2 | 7/2021 | Berme et al. |
| 11,074,711 B1 | 7/2021 | Akbas et al. |
| 11,097,154 B1 | 8/2021 | Berme et al. |
| 11,158,422 B1 | 10/2021 | Wilson et al. |
| 11,182,924 B1 | 11/2021 | Akbas et al. |
| 11,262,231 B1 | 3/2022 | Berme et al. |
| 11,262,258 B2 | 3/2022 | Berme et al. |
| 11,301,045 B1 | 4/2022 | Berme et al. |
| 11,311,209 B1 | 4/2022 | Berme et al. |
| 11,321,868 B1 | 5/2022 | Akbas et al. |
| 11,337,606 B1 | 5/2022 | Berme et al. |
| 11,348,279 B1 | 5/2022 | Akbas et al. |
| 2003/0216656 A1 | 11/2003 | Berme et al. |
| 2008/0228110 A1 | 9/2008 | Berme |
| 2009/0209343 A1 | 8/2009 | Foxlin et al. |
| 2011/0277562 A1 | 11/2011 | Berme |
| 2012/0266648 A1 | 10/2012 | Berme et al. |
| 2012/0271565 A1 | 10/2012 | Berme et al. |
| 2015/0096387 A1 | 4/2015 | Berme et al. |
| 2016/0245711 A1 | 8/2016 | Berme et al. |
| 2016/0334288 A1 | 11/2016 | Berme et al. |
| 2017/0213145 A1 | 7/2017 | Pathak et al. |
| 2018/0024015 A1 | 1/2018 | Berme et al. |
| 2018/0218587 A1 | 8/2018 | Wong et al. |
| 2018/0253152 A1 | 9/2018 | Forsblom et al. |
| 2019/0008417 A1* | 1/2019 | Mazumder ........... A61B 5/1122 |
| 2019/0078951 A1 | 3/2019 | Berme et al. |
| 2019/0282130 A1 | 9/2019 | Dohrmann et al. |
| 2019/0346280 A1 | 11/2019 | Mutschler et al. |
| 2020/0139229 A1 | 5/2020 | Berme et al. |
| 2020/0170510 A1 | 6/2020 | Ferdows et al. |
| 2020/0205697 A1 | 7/2020 | Zheng et al. |
| 2020/0408625 A1 | 12/2020 | Berme et al. |
| 2021/0333163 A1 | 10/2021 | Berme et al. |
| 2022/0178775 A1 | 6/2022 | Berme et al. |

OTHER PUBLICATIONS

Second office action on the merits (Final Rejection) in U.S. Appl. No. 17/141,014, dated Aug. 11, 2021.
Third office action on the merits (Non-Final Rejection) in U.S. Appl. No. 17/141,014, dated Nov. 23, 2021.
Fourth office action on the merits (Final Rejection) in U.S. Appl. No. 17/141,014, dated Mar. 9, 2022.

* cited by examiner

BODY SWAY MEASUREMENT SYSTEM

CROSS-REFERENCE TO RELATED APPLICATIONS

This is a continuation-in-part of U.S. Nonprovisional patent application Ser. No. 17/141,014, entitled "Body Sway Measurement System", filed on Jan. 4, 2021; which claims the benefit of U.S. Provisional Patent Application No. 62/957,178, entitled "Body Sway Measurement System", filed on Jan. 4, 2020, the disclosure of each of which is hereby incorporated by reference as if set forth in their entireties herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a body sway measurement system. More particularly, the invention relates to a body sway measurement system that utilizes a mobile device or other computing device for determining one or more parameters indicative of the body sway of the user.

2. Background

Patients with damage to the inner ear balance system suffer from lack of head-eye coordination. That means, when these patients move their heads, their vision becomes blurry and their balance function deteriorates accordingly. As one example of a cause, damage to the inner ear balance system may occur as a result of the patient sustaining a traumatic brain injury (TBI) or concussion.

In a clinical setting, patients with damaged inner ear balance systems may be tested on a balance plate system in order to assess the degree of impairment. However, when an immediate assessment is needed or desired in a non-clinical setting (e.g., when a return-to-play decision needs to be made on the sidelines at a sporting event), it is typically not feasible to utilize a complex balance plate system. In such an application, it is desirable to employ a simpler and less expensive means for assessing the body sway of the subject.

What is needed, therefore, is a body sway measurement system that is capable of easily determining the body sway of a user in a non-clinical setting. Moreover, a body sway measurement system is needed that does not require complex hardware components, such as a complex balance plate. Furthermore, a need exists for a body sway measurement system that can be used to assess a fall risk of a user and/or whether or not the user has potentially sustained a concussion. In addition, a body sway measurement system is needed that can be used to assess other balance problems, such as those common in older adults.

BRIEF SUMMARY OF EMBODIMENTS OF THE INVENTION

Accordingly, the present invention is directed to a body sway measurement system that substantially obviates one or more problems resulting from the limitations and deficiencies of the related art.

In accordance with one or more embodiments of the present invention, there is provided a body sway measurement system that includes an inertial measurement unit or camera configured to generate time series output data for determining one or more parameters indicative of the body sway of a user; and a mobile device including a data processor, the data processor including at least one hardware component, the data processor being operatively coupled to the inertial measurement unit or camera, the data processor configured to receive the time series output data from the inertial measurement unit or camera, and the data processor and/or a cloud server configured to determine the one or more parameters indicative of the body sway of the user using a trained neural network.

In a further embodiment of the present invention, the data processor and/or the cloud server is configured to determine the one or more parameters indicative of the body sway of the user by inputting the time series output data from the inertial measurement unit or camera into the trained neural network, and utilizing the trained neural network to associate the time series output data with a determinate class so as to generate the one or more parameters indicative of the body sway of the user.

In yet a further embodiment, the trained neural network is selected from the group consisting of: (i) a convolutional neural network (CNN), (ii) an inception network, (iii) an echo state network, (iv) and combinations thereof.

In still a further embodiment, the mobile device is selected from the group consisting of: (i) a smartphone, (ii) a tablet computing device, (iii) a laptop computing device, (iv) a smartwatch, and (v) a head-mounted display.

In yet a further embodiment, the mobile device comprises the inertial measurement unit or the camera configured to generate the output data for determining the one or more parameters indicative of the body sway of the user; and the data processor of the mobile device and/or the cloud server is configured to determine the one or more parameters indicative of the body sway of the user based upon the output data from the inertial measurement unit or the camera.

In still a further embodiment, the inertial measurement unit or the camera configured to generate the output data for determining the one or more parameters indicative of the body sway of the user is located remotely from the mobile device; and the data processor of the mobile device and/or the cloud server is configured to determine the one or more parameters indicative of the body sway of the user based upon the output data from the remotely located inertial measurement unit or camera.

In yet a further embodiment, the one or more parameters indicative of the body sway of the user determined by the data processor of the mobile device are selected from the group consisting of: (i) a sway stability score, (ii) a sway angle of the user, (iii) sway coordinates of the user, (iv) a sway envelope of the user, (v) a sway velocity of the user, and (vi) a sway area of the user.

In still a further embodiment, the data processor of the mobile device and/or the cloud server is further configured to determine a fall risk of the user based upon the one or more parameters indicative of the body sway of the user.

In yet a further embodiment, the body sway measurement system further comprises a visual display device having an output screen, the visual display device operatively coupled to the data processor, and the visual display device configured to display at least one manipulatable element of an interactive game on the output screen so that the at least one manipulatable element is visible to the user; and the data processor is programmed to control the movement of the at least one manipulatable element of the interactive game displayed on the output screen of the visual display device by using the one or more parameters indicative of the body sway of the user, and the data processor is further programmed to determine a fall risk of the user based upon the performance of the user while playing the interactive game.

In still a further embodiment, the body sway measurement system further comprises a visual display device having an output screen, the visual display device operatively coupled to the data processor, and the visual display device configured to display a first object and a second object on the output screen so that the first and second objects are visible to the user; and the data processor is programmed to displace the first object on the output screen of the visual display device, and the data processor is further programmed to control the movement of the second object on the output screen of the visual display device by using the one or more parameters indicative of the body sway of the user so that the user is able to attempt to follow the first object on the output screen with the second object by controlling the movement of the second object based upon his or her body sway.

In yet a further embodiment, the mobile device comprises the inertial measurement unit and the camera configured to generate the output data for determining the one or more parameters indicative of the body sway of the user; and the data processor of the mobile device and/or the cloud server is configured to determine the one or more parameters indicative of the body sway of the user based upon the output data from both the inertial measurement unit and the camera.

In accordance with one or more other embodiments of the present invention, there is provided a body sway measurement system that includes an inertial measurement unit or camera configured to generate time series output data for determining one or more parameters indicative of the body sway of a user; and a computing device including a data processor, the data processor including at least one hardware component, the data processor being operatively coupled to the inertial measurement unit or camera, the data processor configured to receive the time series output data from the inertial measurement unit or camera, and the data processor and/or a cloud server configured to determine the one or more parameters indicative of the body sway of the user using a trained neural network.

In a further embodiment of the present invention, the data processor and/or the cloud server is configured to determine the one or more parameters indicative of the body sway of the user by inputting the time series output data from the inertial measurement unit or camera into the trained neural network, and utilizing the trained neural network to associate the time series output data with a determinate class so as to generate the one or more parameters indicative of the body sway of the user.

In yet a further embodiment, the trained neural network is selected from the group consisting of: (i) a convolutional neural network (CNN), (ii) an inception network, (iii) an echo state network, (iv) and combinations thereof.

In still a further embodiment, the computing device is selected from the group consisting of: (i) a desktop computing device, (ii) a tower computing device, (iii) a server computing device, (iv) a small-form-factor personal computer, (v) a smartphone, (vi) a tablet computing device, (vii) a laptop computing device, and (viii) a smartwatch.

In yet a further embodiment, the computing device comprises the inertial measurement unit or the camera configured to generate the output data for determining the one or more parameters indicative of the body sway of the user; and the data processor of the computing device and/or the cloud server is configured to determine the one or more parameters indicative of the body sway of the user based upon the output data from the inertial measurement unit or the camera.

In still a further embodiment, the inertial measurement unit or the camera configured to generate the output data for determining the one or more parameters indicative of the body sway of the user is located remotely from the computing device; and the data processor of the computing device and/or the cloud server is configured to determine the one or more parameters indicative of the body sway of the user based upon the output data from the remotely located inertial measurement unit or camera.

In yet a further embodiment, the one or more parameters indicative of the body sway of the user determined by the data processor of the computing device are selected from the group consisting of: (i) a sway stability score, (ii) a sway angle of the user, (iii) sway coordinates of the user, (iv) a sway envelope of the user, (v) a sway velocity of the user, and (vi) a sway area of the user.

In still a further embodiment, the data processor of the computing device and/or the cloud server is further configured to determine a fall risk of the user based upon the one or more parameters indicative of the body sway of the user.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

The present invention is described herein, in an exemplary manner, with reference to computer system architecture and exemplary processes carried out by the computer system. In one or more embodiments, the functionality described herein can be implemented by computer system instructions. These computer program instructions may be loaded directly onto an internal data storage device of a computing device (e.g., an internal data storage device of a smartphone or laptop computing device). Alternatively, these computer program instructions could be stored on a portable computer-readable medium (e.g., a flash drive, etc.), and then subsequently loaded onto a computing device such that the instructions can be executed thereby. In other embodiments, these computer program instructions could be embodied in the hardware of the computing device, rather than in the software thereof. It is also possible for the computer program instructions to be embodied in a combination of both the hardware and the software.

This description describes in general form the computer program(s) required to carry out the body sway analysis for a user. Any competent programmer in the field of information technology could develop a system using the description set forth herein.

For the sake of brevity, conventional computer system components, conventional data networking, and conventional software coding will not be described in detail herein. Also, it is to be understood that the connecting lines shown in the block diagram(s) included herein are intended to represent functional relationships and/or operational couplings between the various components. In addition to that which is explicitly depicted, it is to be understood that many alternative or additional functional relationships and/or physical connections may be incorporated in a practical application of the system.

Figure 1:
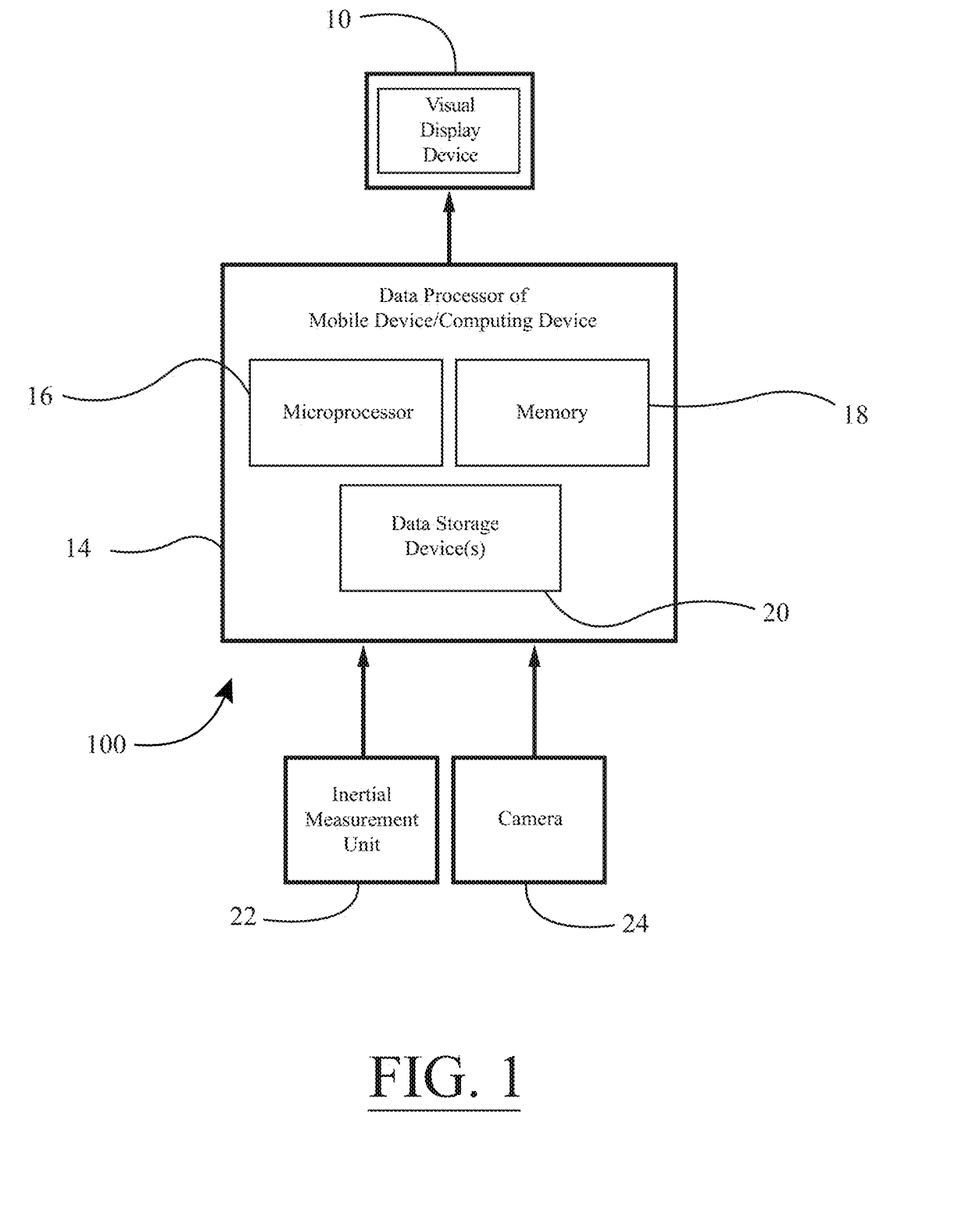
FIG. 1 is a block diagram of constituent components that may be utilized in an illustrative embodiment of the body sway measurement system described herein.

An illustrative embodiment of a body sway measurement system is seen generally at 100 in FIG. 1. In the illustrative embodiment, the body sway measurement system 100 generally comprises a visual display device 10 and a data processor 14 (e.g., a data processor of a computing device, such as a mobile device). Also, as shown in FIG. 1, the body sway measurement system 100 further comprises at least one of an inertial measurement unit 22 and camera 24 operatively coupled to the data processor 14, the inertial measurement unit 22 and/or the camera 24 is configured to generate output data for determining one or more parameters indicative of the body sway of a user. In the illustrative embodiment, the data processor 14 is configured to receive the output data from the inertial measurement unit 22 and/or camera 24, and to determine the one or more parameters indicative of the body sway of the user. In the illustrative embodiment, the inertial measurement unit 22 comprises at least one of an accelerometer configured to detect linear acceleration and a gyroscope configured to detect angular velocity. For example, in the illustrative embodiment, the inertial measurement unit 22 may comprise a 3-axis accelerometer, a 3-axis gyroscope and a 3-axis magnetometer to enable the use of motion fusion algorithms. For the motion fusion algorithms, nine (9) degrees of freedom are needed. In this example, the data processor uses square root formula(s) and/or a principal component analysis (PCA) to determine the sway score of the user from the accelerometer, gyroscope, and magnetometer output data.

In one illustrative embodiment, the mobile device with the data processor 14 is selected from the group consisting of: (i) a smartphone, (ii) a tablet computing device, (iii) a laptop computing device, (iv) a smartwatch, and (v) a head-mounted display. For example, in the illustrative embodiment, the inertial measurement unit 22 and/or camera 24 of the body sway measurement system 100 may comprise the built-in inertial measurement unit and/or camera of a smartphone. In another illustrative embodiment, rather than a mobile computing device, another type of computing device is used. For example, the other type of computing device may be a desktop computing device, a tower computing device, a server computing device, or a small-form-factor personal computer. In yet another illustrative embodiment, the sway of the user may be analyzed by an inertial measurement unit on the chest of the user or by the inertial measurement unit present in a head-mounted display.

Figure 4:
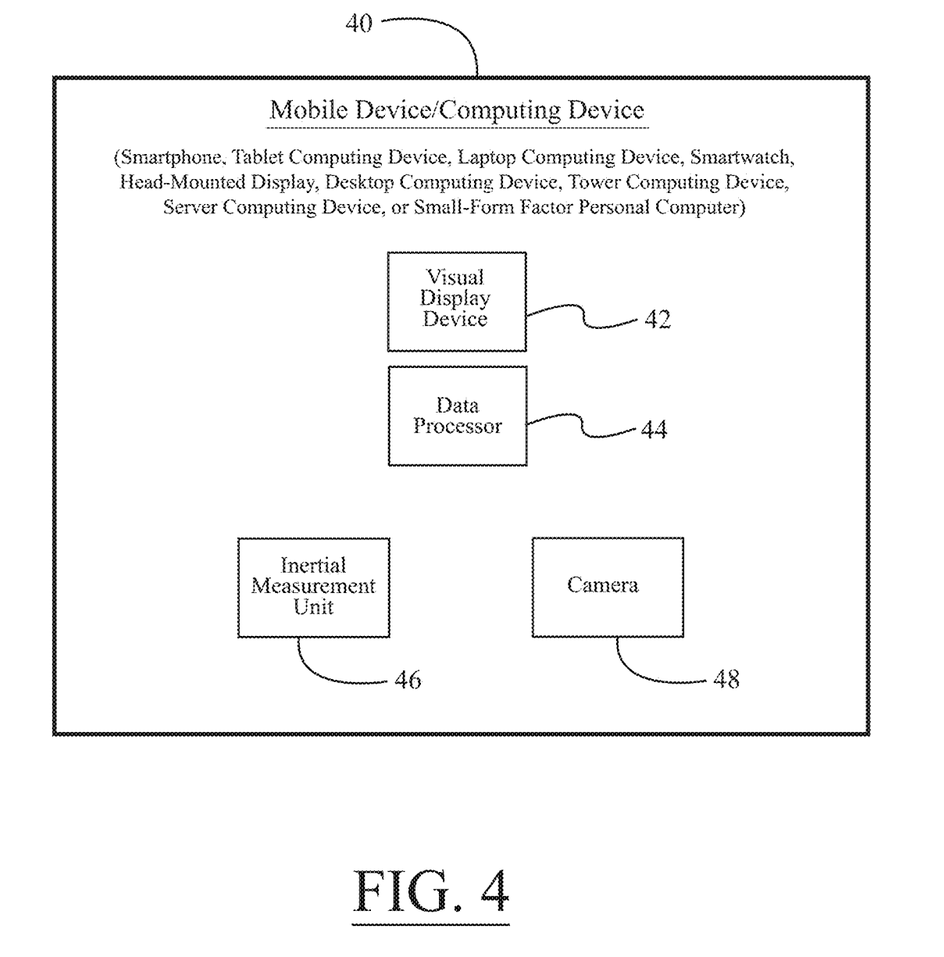
FIG. 4 is a block diagram of constituent components of one illustrative body sway measurement system, where the mobile device or computing device comprises an integral inertial measurement unit and camera.

In FIG. 4, an illustrative body sway measurement system comprising a mobile device or computing device 40 with a built-in inertial measurement unit 46 and a built-in camera 48 is diagrammatically represented. The built-in inertial measurement unit 46 and camera 48 are operatively coupled to the data processor 44 of the mobile device or computing device 40. Also, as shown in FIG. 4, the mobile device or computing device 40 also may include a built-in visual display device 42 (e.g., the touchscreen of a smartphone or the display of a head-mounted display) that is operatively coupled to the data processor 44 of the mobile device or computing device 40.

As shown in the illustrative block diagram of FIG. 1, the data processor 14 (e.g., the data processor 14 of the mobile device or other computing device) of the body sway measurement system 100 comprises a microprocessor 16 for processing data, memory 18 (e.g., random access memory or RAM) for storing data during the processing thereof, and data storage device(s) 20, such as one or more internal solid state drives, external flash drives, or any combination thereof. As shown in FIG. 1, the visual display device 10 is operatively coupled to the data processor 14 such that data is capable of being transferred between these devices (e.g., the visual display device 10 may be a built-in touchscreen user interface of a mobile device).

In the illustrative embodiment, the body sway measurement system 100 is in the form of a mobile sway measurement system for easily performing a sway analysis in a variety of different locations. As described in further detail below, the body sway measurement system 100 may comprise a remote attachable movement sensor (i.e., a remote inertial measurement unit 22) in operative communication with the mobile device or the inertial measurement unit 22 may comprise the built-in inertial measurement unit (IMU) of the mobile device (e.g., the smartphone). In the illustrative embodiment, the body sway measurement system 100 may provide haptic and auditory feedback for the user based upon the one or sway parameters determined by the data processor 14. As an alternative, the body sway measurement system 100 may comprise an optical motion capture system that utilizes a camera 24 (either the built-in camera of the mobile device or a remote camera) to capture image data for determining the one or more parameters indicative of the body sway of a user. Also, in the illustrative embodiment, camera optical object stabilization may be used to stabilize the recorded image of the camera 24 by varying the optical path to the sensor.

In a first variation of the illustrative embodiment, the mobile device (e.g., the smartphone) comprises the inertial measurement unit 22 configured to generate the output data for determining the one or more parameters indicative of the body sway of the user (i.e., the built-in inertial measurement unit of the smartphone is utilized). In this first variation of the illustrative embodiment, the data processor 14 of the mobile device is configured to determine the one or more parameters indicative of the body sway of a user based upon the output data from the inertial measurement unit 22.

For example, as part of the sway analysis, the inertial measurement unit 22 (i.e., IMU 22) is capable of measuring gravitational and motion components. The gravitational component makes it possible to define a true vertical vector. The body sway is the angle and translation made by the IMU 22 around that true vertical. The calculation for the body sway can be done by a principal component analysis (PCA) to approximate the area of body sway excursion (i.e., the body sway envelope) as follows:

$$\sigma_{xy}^2 = \frac{1}{N-1} \sum_{i=1}^{N} (x_i - \bar{x})(y_i - \bar{y}) \quad (1)$$

$$\tan\theta = \frac{\sigma_{xy}^2}{\sigma_0^2 - \sigma_{xy}^2} \quad (2)$$

where $\theta$ in equation (2) above is the body sway angle. In the illustrative embodiment, the computation of the principal component analysis (PCA) set forth in equation (1) may be computed for each joint of the user.

In a second variation of the illustrative embodiment, the inertial measurement unit 22 that is configured to generate the output data for determining the one or more parameters indicative of the body sway of the user is located remotely from the mobile device. In this second variation of the illustrative embodiment, the data processor 14 of the mobile device is configured to determine the one or more parameters indicative of the body sway of a user based upon the output data from the remotely located inertial measurement unit 22. In the illustrative embodiment, the data processor 14 may be operatively coupled to the remotely located inertial measurement unit 22 by a wireless connection.

In the second variation of the illustrative embodiment, a plurality of inertial measurement units 22 located remotely from the mobile device may be used to track the positions of multiple limbs of the user. For example, a first one of the inertial measurement units 22 may be mounted on the first leg of the user (i.e., a left leg), a second one of the inertial measurement units 22 may be mounted on the second leg of the user (i.e., a right leg), a third one of the inertial measurement units 22 may be mounted on the first arm of the user (i.e., a left arm), and a fourth one of the inertial measurement units 22 may be mounted on the second arm of the user (i.e., a right arm). In this illustrative embodiment, the data processor 14 may use the output data from the inertial measurement units 22 for self-identification and/or intrinsic calibration of the inertial measurement units 22. In particular, the data processor 14 may use the positional coordinates outputted by the inertial measurement units 22 to automatically determine which limb the particular inertial measurement unit 22 is attached to (e.g., based on the positional coordinates outputted by the inertial measurement units 22, the data processor 14 is able to determine the left or right orientation of the leg or arm, the front or back orientation of the leg or arm, and determine whether the inertial measurement unit 22 is located on an arm or a leg). Also, the data processor 14 may use the angular data outputted by the inertial measurement units 22 to automatically determine which limb the particular inertial measurement unit 22 is attached to (e.g., when the inertial measurement unit 22 is attached to an arm, rather than the leg, the angular displacement of the inertial measurement unit 22 will be greater because the arm swing angle is greater). Also, when the user swings his or her arms, the angular displacements of the inertial measurement units 22 attached to the arms will be greater in the forward arm swing direction as compared to the rearward arm swing direction. Similarly, when the user walks or runs, the angular displacements of the inertial measurement units 22 attached to the legs will be greater in the forward direction as compared to the rearward direction. As such, the pattern of movement of the user and/or the positional coordinates outputted by the inertial measurement units 22 may be used for self-identification of the inertial measurement units 22. For example, using the pattern of movement of the user and/or the positional coordinates of the inertial measurement units 22, the data processor 14 may identify a front or back orientation of the inertial measurement unit 22, a left or right orientation of the inertial measurement unit 22, and/or whether the inertial measurement unit 22 is attached to a lower limb or an upper limb of the user.

When the inertial measurement units 22 are being used for the live analysis or streaming analysis of the movement of the user, a pre-calibration routine may be performed by the data processor 14 where the self-identification of the inertial measurement units 22 is performed beforehand. When the output data from the inertial measurement units 22 is processed after data collection (i.e., post-processing of the output data), a dynamic calibration routine may be performed by the data processor 14 where the self-identification of the inertial measurement units 22 is performed during data collection (i.e., on-the-fly calibration).

In the illustrative embodiment, the IMU self-identification process may comprise the following three steps for a pre-calibration routine. First, the user may attach the inertial measurement units 22 to his or her body (i.e., one IMU on each arm and one IMU on each leg). Secondly, the user may start walking or take two or more steps in place to calibrate the inertial measurement units 22. Finally, using a model of the user and IMU quaternion and positional data, the data processor 14 automatically detects the inertial measurement units 22 and self-identifies their locations on the user's right and left arms and the user's right and left legs.

As one example, in the first and second variations of the illustrative embodiment, the data processor of the mobile device or computing device may read a stream of data from the IMU. Then, the data processor may combine data from different axes or can use combined data (x, y, z), i.e., look at motion (displacement and rotation) along the three planes. After which, the data processor applies a sway algorithm to determine the sway stability score. In this example, the best placement of the IMU is around the CoM of the subject (the waist area), but can be also placed on the individual's head. Also, in this example, x-y plane data can be used to look at the horizontal displacement only. In this example, the IMU can be wired or wireless (i.e., communicate by Bluetooth® or WiFi®). The wireless data transfer rate is slower, but is adequate. Also, in this example, one can run this same x-y-z data stream to a CNN model to process the data instead of using calculated/programmed logic.

In the first and second variations of the illustrative embodiment, where the data processor of the mobile device or computing device reads a stream of data from the IMU, the data processor is configured to receive the time series output data from the inertial measurement unit, and then the data processor and/or a cloud server is configured to determine the one or more parameters indicative of the body sway of the user using a trained neural network. More specifically, the data processor and/or the cloud server is configured to determine the one or more parameters indicative of the body sway of the user by inputting the time series output data from the inertial measurement unit into the trained neural network, and utilizing the trained neural network to associate the time series output data with a determinate class so as to generate the one or more parameters indicative of the body sway of the user. The time series output data for the IMU may comprise accelerometer time series output data (e.g., pitch, roll) and gyroscope data (e.g., pitch, roll, yaw) for a given time duration. In addition, one or more force dimensions may be used in the training and classification of the neural network. As one example, the one or more parameters indicative of the body sway of the user determined by the neural network may comprise a sway stability score defined on a particular scale (e.g., 0-Poor to 9-Excellent). Initially, a dataset for each set of output class is collected and the neural network is trained. The neural network is trained on the IMU data (roll, pitch, yaw, etc.) that is collected. Then, after the training of the network, the neural network outputs a sway stability score (e.g., 0-Poor to 9-Excellent) for a new data input matching the dimensionality of the training input (i.e., during inference). In the illustrative embodiment, a dataset is defined as a collection of pairs (e.g., stream of time series raw IMU output data, score class), which means that to each time series of raw IMU output data is associated a determinate class. Given a dataset, the neural network solves a classification problem by associating to a new IMU data set, with generally the same structure as the other previously classified IMU data sets, the probability that the new IMU data set belongs to a particular one of the classes, according to the features of the previous IMU data sets associated to each class. In the illustrative embodiment, the IMU data set may comprise a univariate time series with one ordered set of real values (e.g., accelerometer pitch data), or a M dimensional multivariate time series consisting of M different univariate time series with the same length (e.g., accelerometer pitch data, accelerometer roll data, gyroscope pitch data, gyroscope roll data, gyroscope yaw data). In the illustrative embodiment, the time series classification problem solved by the neural network is performed on the univariate time series (e.g., accelerometer pitch data) or multivariate time series (e.g., accelerometer pitch data, accelerometer roll data, gyroscope pitch data, gyroscope roll data, gyroscope yaw data).

In the illustrative embodiment, during the training of the neural network, the relationship between the sway stability score and a particular IMU time series data set is determined. For example, during the training of the neural network, the sway stability score may be determined for a particular subject based upon ground truth data from a force plate or balance plate while an IMU data set is being acquired using an IMU, then that particular IMU data set is able to be associated with a particular scale (e.g., 0-Poor to 9-Excellent) of the sway stability score.

In the illustrative embodiment, the trained neural network utilized by the data processor and/or the cloud server may be selected from the group consisting of: (i) a convolutional neural network (CNN), (ii) an inception network, (iii) an echo state network, (iv) and combinations thereof.

In the illustrative embodiment, when the trained neural network comprises a convolutional neural network (CNN), the convolutional neural network (CNN) receives the time series output data as an input, is able to successfully capture the spatial and temporal patterns through application trainable filters, and assigns importance to these patterns using trainable weights. Advantageously, the convolutional neural network (CNN) has the ability to learn filters, rather than requiring the filters to be engineered by hand.

In the illustrative embodiment, when the trained neural network comprises an inception network, the inception network receives the time series output data as an input, and processes the data using inception modules, rather than the convolution layers and pooling layers used by the convolutional neural network (CNN).

In the illustrative embodiment, when the trained neural network comprises an echo state network, the echo state network receives the time series output data as an input, and processes the time series output data using neuron-like nodes which are organized into an input layer, hidden layers, a dimension reduction layer, and an output layer. The echo state network is a type of recurrent neural network where each connection between neurons has a corresponding trainable weight. As one example, the dimension reduction layer can be a tensor principal component analysis (PCA) for multivariate time series data.

In the illustrative embodiment, a principal component analysis (PCA) may be applied on IMU (e.g., roll, pitch, yaw) univariate and multivariate data for dimensionality reduction making "class" identification easier by the CNN or other type of neural network that is utilized. For example, the dimension reduction layer of an echo state network may utilize the PCA for multivariate time series data dimension reduction.

In a third variation of the illustrative embodiment, the mobile device (e.g., the smartphone) comprises the camera 24 configured to generate the output data for determining the one or more parameters indicative of the body sway of the user (i.e., the built-in camera 24 of the smartphone is utilized). For example, the mobile device (e.g., the smartphone) may be attached to the user by means of a strap, and the camera 24 of the mobile device may be focused on a remote stationary target. As the user's body moves due to his or her sway, the position of the remote target changes in the image captured by the camera 24 so that the one or more parameters indicative of the body sway of the user may be determined from the image data of the camera 24. In another variation of the illustrative embodiment, the one or more parameters indicative of the body sway of the user may be determined based upon a combination of the image data captured by the camera 24 of the mobile device and the output data of the inertial measurement unit 22 of the mobile device.

In a fourth variation of the illustrative embodiment, the camera 24 that is configured to generate the output data for determining the one or more parameters indicative of the body sway of the user is located remotely from the mobile device. In this fourth variation of the illustrative embodiment, the data processor 14 of the mobile device is configured to determine the one or more parameters indicative of the body sway of a user based upon the output data from the remotely located camera 24. In the illustrative embodiment, the data processor 14 may be operatively coupled to the remotely located camera 24 by a wireless connection.

In this fourth variation of the illustrative embodiment, the data processor 14 of the mobile device is configured to determine the one or more parameters indicative of the body sway of the user based upon the output data from the camera 24 using pose estimation. For example, as part of the sway analysis, the camera 24 is capable of capturing image data of the user. Then, the data processor 14 receives the image data of the user from the camera 24. After receiving the image data, the data processor 14 may then extract features from the image data for providing inputs to a convolutional neural network (CNN). After this step, the data processor 14 may generate one or more keypoints using a keypoint subnet, and determine one or more poses of the user based upon the position of the keypoints. In one or more embodiments, when a plurality of cameras 24 are used to capture the movement of the user, the data processor 14 may generate one or more volumetric heatmaps using the convolutional neural network, and then apply a maximization function to the one or more volumetric heatmaps to obtain a three dimensional pose data of one or more persons in the scene. In the illustrative embodiment, the data processor 14 may be configured to determine the one or more parameters indicative of the body sway of the user from the aforedescribed pose estimation data. In this fourth variation of the illustrative embodiment, the pose estimation system may comprise the 3D pose estimation system described in U.S. Pat. No. 10,853,970, the entire disclosure of which is incorporated herein by reference.

Figure 6:
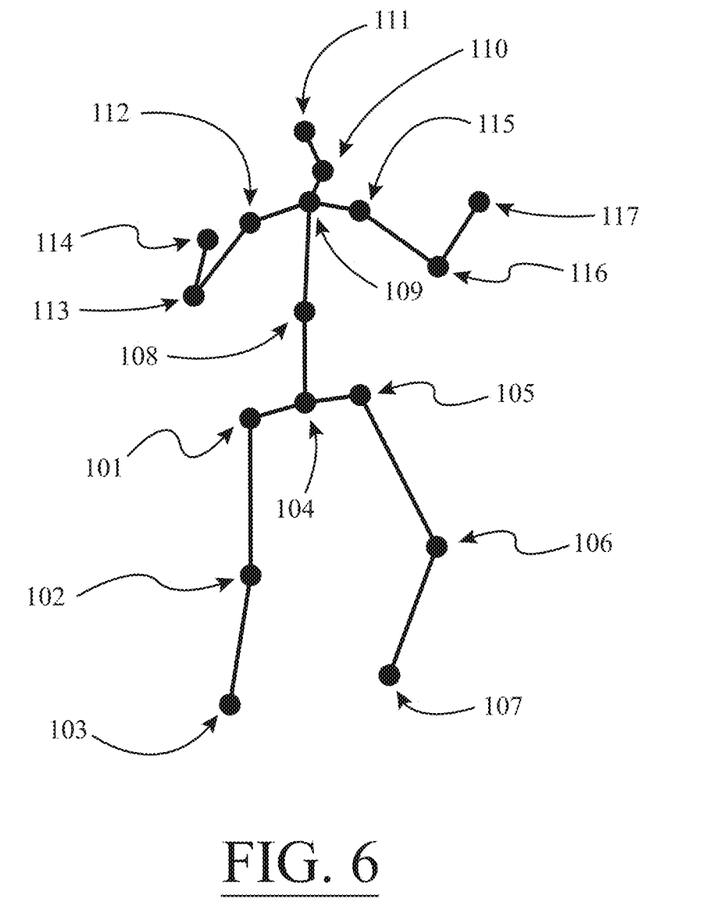
FIG. 6 illustrates keypoint locations for camera-based pose determination performed by the body sway measurement system.

In the fourth variation of the illustrative embodiment, where the data processor of the mobile device or computing device reads a stream of image data from the camera 24, the data processor is configured to receive the time series output data from the camera 24, and then the data processor and/or a cloud server is configured to determine the one or more parameters indicative of the body sway of the user using a trained neural network. More specifically, the data processor and/or the cloud server is configured to determine the one or more parameters indicative of the body sway of the user by inputting the time series output data from the camera 24 into the trained neural network, and utilizing the trained neural network to associate the time series output data with a determinate class so as to generate the one or more parameters indicative of the body sway of the user. The time series output data for the camera 24 may comprise camera-based pose estimated keypoint data (e.g., markered or markerless). FIG. 6 depicts exemplary keypoint locations for a body of a user, which are defined as follows:

- 101 Right Hip 110 Neck Base
- 102 Right Knee 111 Center Head
- 103 Right Foot 112 Right Shoulder
- 104 Bottom Torso 113 Right Elbow
- 105 Left Hip 114 Right Hand
- 106 Left Knee 115 Left Shoulder
- 107 Left Foot 116 Left Elbow
- 108 Center Torso 117 Left Hand
- 109 Upper Torso For input into neural network, one may select a single keypoint on the body such as center torso (108) or a series of keypoints, such as main spine line (111, 110, 109, 108, 104) or the whole body keypoints (101 to 117). As one example, the one or more parameters indicative of the body sway of the user determined by the neural network may comprise a sway stability score or body sway profile/pattern defined on a particular scale (e.g., 0-Poor to 9-Excellent). Initially, a dataset for each set of output class is collected and the neural network is trained. The neural network may be trained on keypoint data collected using markered or markerless motion capture techniques. Then, after the training of the network, the neural network outputs a body sway profile/pattern or sway stability score (e.g., 0-Poor to 9-Excellent) for a new data input matching the dimensionality of the training input (i.e., during inference). In the illustrative embodiment, a dataset is defined as a collection of pairs (e.g., stream of time series keypoint output data, score class), which means that to each time series of keypoint output data is associated a determinate class. Given a dataset, the neural network solves a classification problem by associating to a new keypoint data set, with generally the same structure as the other previously classified keypoint data sets, the probability that the new keypoint data set belongs to a particular one of the classes, according to the features of the previous keypoint data sets associated to each class. In the illustrative embodiment, the keypoint data set may comprise a univariate time series with one ordered set of real values (e.g., single keypoint data), or a M dimensional multivariate time series consisting of M different univariate time series with the same length (e.g., multiple keypoint data). In the illustrative embodiment, the time series classification problem solved by the neural network is performed on the univariate time series (e.g., single keypoint data) or multivariate time series (e.g., multiple keypoint data).

In the illustrative embodiment, during the training of the neural network, the relationship between the sway stability score and a particular kepoint time series data set is determined. For example, during the training of the neural network, the sway stability score may be determined for a particular subject based upon ground truth data from a force plate or balance plate while a keypoint data set is being acquired using the camera 24, then that particular keypoint data set is able to be associated with a particular scale (e.g., 0-Poor to 9-Excellent) of the sway stability score.

In the illustrative embodiment, the trained neural network utilized by the data processor and/or the cloud server may be selected from the group consisting of: (i) a convolutional neural network (CNN), (ii) an inception network, (iii) an echo state network, (iv) and combinations thereof.

Also, in the illustrative embodiment, using the pose estimation described above, the data processor 14 may determine a displacement curve for any of the keypoints of the user (e.g., a displacement curve for the shoulder joint, elbow joint, knee joint, ankle joint, etc.).

As another example, in this fourth variation of the illustrative embodiment, the data processor of the mobile device or computing device may read a streamed sequence of video frames containing the user or subject. Multiple sequential frames (e.g., 30,000 frames spanning 30 seconds) are needed (e.g., 30 seconds to a minute). Then, a trained CNN is used by the data processor to find the center of mass, CoM (or center of gravity, CoG) in 3D coordinate space. After which, a sway algorithm is used by the data processor to determine the stability of the subject (i.e., the stability score of the subject). Also, in this example, an additional CNN model may be used to process the 3D CoM/CoG data to provide the stability score instead of using calculated/programmed logic. A single camera may be used, but multiple cameras also may be used for more accuracy (i.e., the CoM/CoG estimation with a CNN is more accurate with multiple cameras). The camera is generally placed in front of the subject, but the arrangement can vary if multiple cameras are used. Also, with additional training and refinement of the CNN, the stability score can be estimated with a smaller number of frames (e.g., 5 seconds of video data at 60 frames per second).

In the illustrative embodiment, as described above, the one or more parameters indicative of the body sway of the user determined by the neural network may comprise a sway stability score defined on a particular scale (e.g., 0-Poor to 9-Excellent). The neural network may be trained using calculated or collected force data (Fx,Fy,Fz, CoM, CoG, etc.). Then, after the training of the network, the neural network outputs a sway stability score (e.g., 0-Poor to 9-Excellent) for a new data input matching the dimensionality of the training input (i.e., during inference).

In the illustrative embodiment, in addition to the sway stability score defined on a particular scale (e.g., 0-Poor to 9-Excellent), other assessment parameters (neural network output classes) for the user may include: (i) fall risk prediction (0-Normal, 1-Fall Risk Above Normal), (ii) fall risk on a scale (0-Normal to 9-High Fall Risk), (iii) normality of gait (0-Normal Gait, 1-Abnormal Gait), and (iv) type of fall risk strategy (0-Hip-Fall-Risk Strategy, 1-Foot-Fall-Risk-Strategy).

Also, in the illustrative embodiment, other sources of input time series data for the neural network may include (i) force plate data (e.g., Fx, Fy, Fz, Mx, My, Mz, CoPx, CoPy, etc.), and (ii) balance plate data (e.g., Fx, Fy, Fz, CoPx, CoPy, etc.). That is, in the illustrative embodiment, one or more force dimensions or their derivatives like CoG (center of gravity)/CoM (Center of Mass)/CoMM (Center of Mass Moments) may be used in the training and classification using the neural networks (e.g., CNNs).

Figure 5:
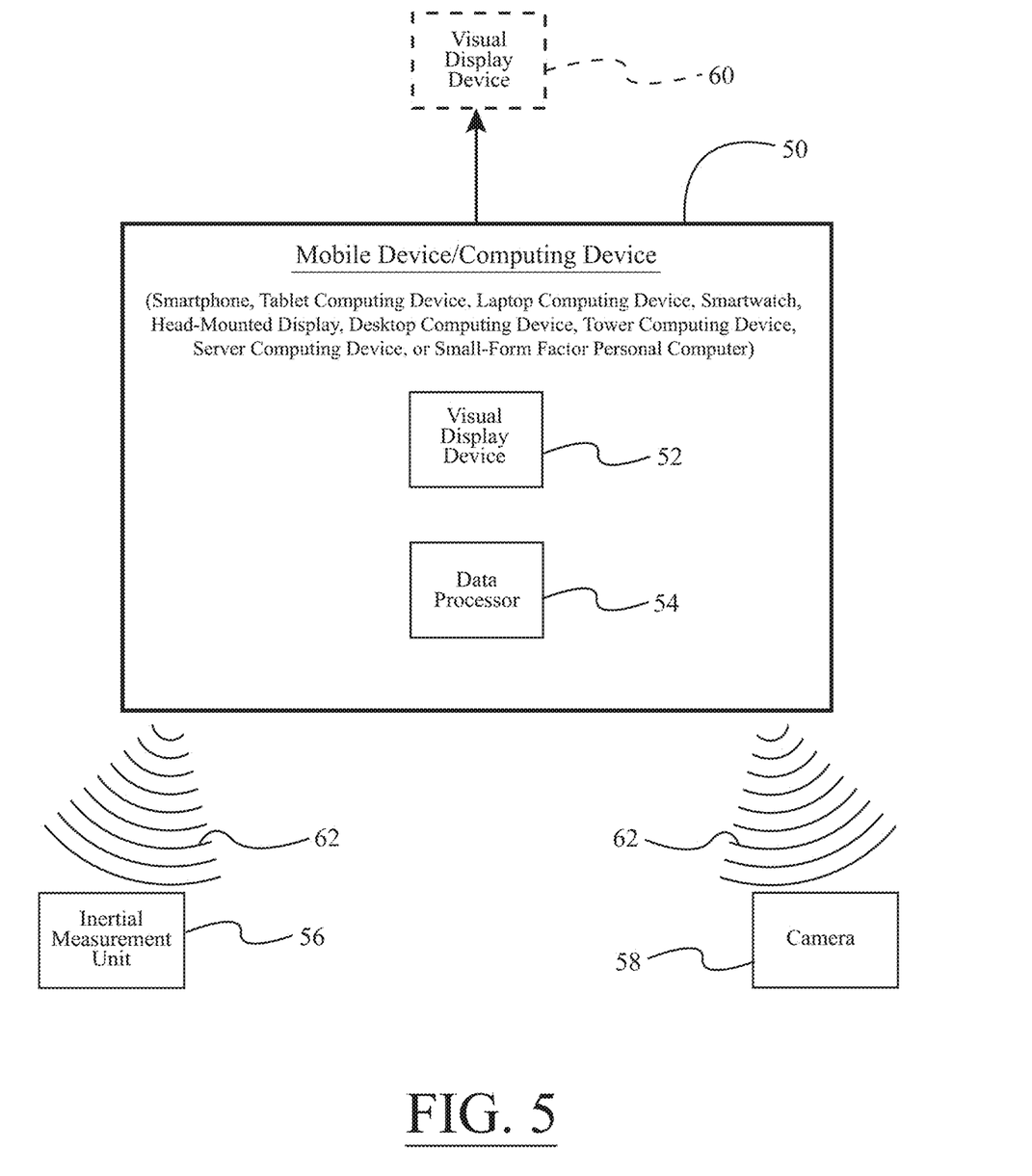
FIG. 5 is a block diagram of constituent components of another illustrative body sway measurement system, where the inertial measurement unit and camera are located remotely from the mobile device or computing device.

In FIG. 5, an illustrative body sway measurement system comprising a mobile device or computing device 50 operatively coupled to a remotely located inertial measurement unit 56 and a remotely located camera 58 by a wireless connection 62 is diagrammatically represented. The remotely located inertial measurement unit 56 and camera 58 are operatively coupled to the data processor 54 of the mobile device or computing device 50 by wireless connection means 62, such as a personal area network (PAN) or local area network (LAN). Also, as shown in FIG. 5, the mobile device or computing device 50 also may include a built-in visual display device 52 (e.g., the touchscreen of a smartphone or the display of a head-mounted display) that is operatively coupled to the data processor 54 of the mobile device or computing device 50. As also shown in FIG. 5, in addition to, or as an alternative to the built-in visual display device 52, the mobile device or computing device 50 may comprises a remotely located visual display device 60.

In the illustrative embodiment, the data acquired by the inertial measurement unit 22 and/or the camera 24 of the mobile device (e.g., the smartphone) may be recorded and processed in a mobile application (i.e., the data may be processed locally on the smartphone). Alternatively, the data acquired by the inertial measurement unit 22 and/or the camera 24 of the mobile device (e.g., the smartphone) may be processed remotely on a cloud server (e.g., the pose estimation may be processed remotely), and then displayed on the mobile device using a mobile application. Also, in the illustrative embodiment, the data acquired may be accessible online throughout a cloud-based system.

In the embodiments where a cloud server is used for processing the data acquired by the inertial measurement unit 22 and/or the camera 24 of the mobile device, the data processor of the mobile device may be used for single instance processing and classification of a test input time series data capture, while cloud processing may be used for further classification of the input sequence with higher dimensional data sets, such as for building, comparing and classifying of the class profile over a period of time (e.g., daily, monthly, or yearly). Advantageously, the cloud processing allows for the comparing of data of different users in real-time distributed in different geographical regions.

In the illustrative embodiment, the mobile device may be programmed (by means of the mobile application) to provide both audio and haptic feedback to the user regarding his or her body sway performance (i.e., an audial or tactile warning may be given to the user if the mobile device determines the body sway of the user is abnormally high, which could potentially result in a fall).

Figure 2:
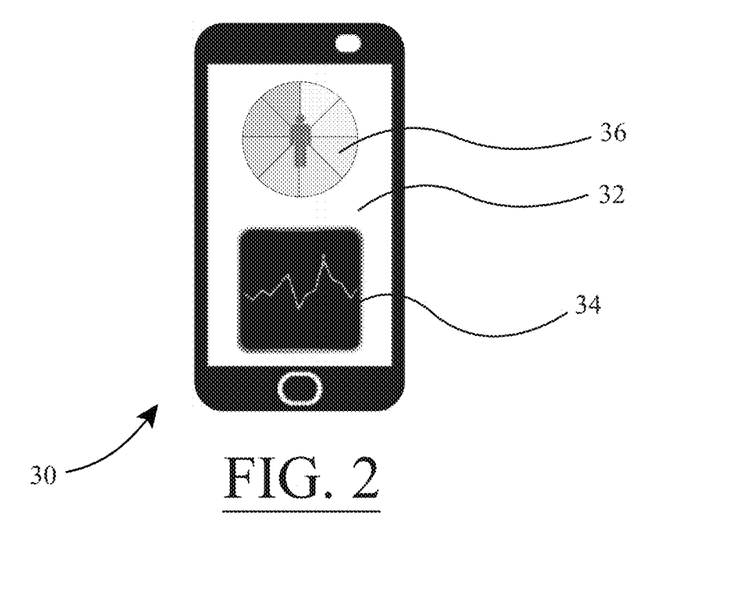
FIG. 2 is a schematic illustration of body sway output information that may be displayed on a smartphone screen of the body sway measurement system.
Figure 3:
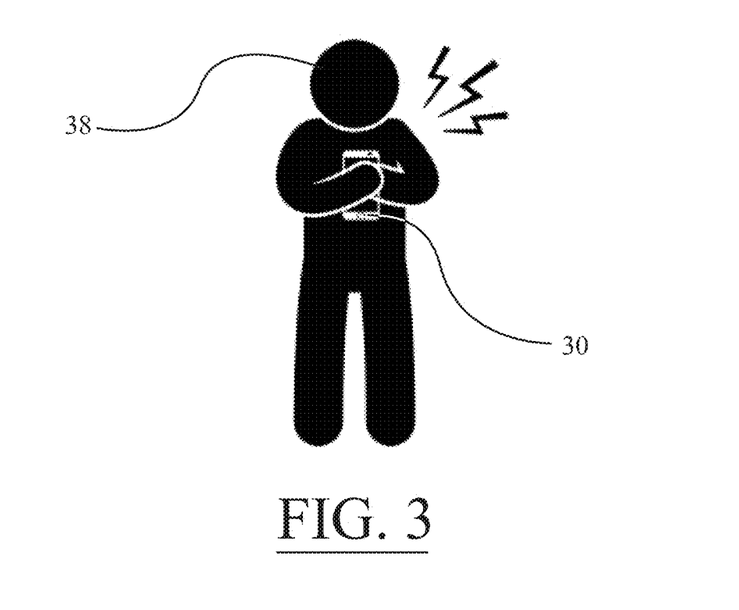
FIG. 3 is a schematic illustration of a user holding a smartphone while the body sway of the user is being measured by the body sway measurement system.

In the illustrative embodiment, the data processor 14 further may be programmed to generate a body sway measurement report with various parameters determined from the output data of the inertial measurement unit 22 and/or the camera 24. For example, the data processor 14 of the mobile device may be programmed to generate and display graphs and other data pertinent to the body sway of the user on the visual display (i.e., touchscreen user interface) of the mobile device (see e.g., FIG. 2). The other data pertinent to the body sway of the user may include body sway parameters, such as: (i) the sway angle of the user, (ii) sway coordinates of the user, (iii) the sway envelope of the user, (iv) a sway velocity of the user, and (v) a sway area of the user. For example, as shown in FIG. 2, the data processor of the smartphone 30 may be programmed to generate and display graphs 34 and other data 36 pertinent to the body sway of the user on the visual display 32. In addition, the data processor 14 of the mobile device may be programmed to track the progress of the user over time (i.e., determine the manner in which the user's body sway changes over time). As explained above, the body sway data may be generated based upon output data from four (4) different sources: (i) an inertial measurement unit 22 of the mobile device, (ii) a remote inertial measurement unit 22, (iii) one or more remote cameras 24 (i.e., one or more remote cameras 24 looking at the user), and (iv) a camera 24 of the mobile device (e.g., when the user 38 is holding the mobile device, such as smartphone 30, as shown in FIG. 3, and the camera 24 of the mobile device is used to determine the movement of the user relative to a fixed object located remotely).

Also, in the illustrative embodiment, the data processor 14 of the mobile device may be further configured to determine a fall risk of the user based upon the one or more parameters indicative of the body sway of a user (e.g., if the sway envelope of the user is outside a predetermined area, then data processor 14 may determine that the user is likely to fall).

In the illustrative embodiment, the body sway measurement system 100 may further comprise a remote visual display device having an output screen (e.g., a remote wall-mounted monitor or television facing the user) operatively coupled to the data processor 14. The remote visual display device may be configured to display at least one manipulatable element (e.g., an airplane) of an interactive game on the output screen so that the at least one manipulatable element is visible to the user. In the illustrative embodiment, the data processor 14 may be programmed to control the movement of the at least one manipulatable element (e.g., an airplane) of the interactive game displayed on the output screen of the visual display device by using the one or more parameters indicative of the body sway of the user (e.g., if the user leans forward, the airplane decreases in altitude, while, if the user leans backward, the airplane increases in altitude). In the exemplary interactive game, the fore/aft leaning of the user could guide the airplane through rings or hoops located at different altitudes in the sky. In the illustrative embodiment, the data processor 14 may be further programmed to determine the fall risk of the user based upon the performance of the user while playing the interactive game (e.g., in the airplane game, the fall risk of the user may increase as the number of rings or hoops missed by the user increases).

In a further embodiment, the body sway measurement system 100 also may include an eye movement tracking device in order to analyze the movement of the user's eyes while the user is focusing on a particular object. For example, if the eye movement tracking device measures erratic eye movements while the user is undergoing a body sway analysis, then the user may have sustained a concussion prior to being tested.

It is readily apparent that the body sway measurement system 100 described above offers numerous advantages and benefits. First, the body sway measurement system 100 is capable of easily determining the body sway of a user in a non-clinical setting. Moreover, the body sway measurement system 100 does not require complex hardware components, such as a complex balance plate. Furthermore, the body sway measurement system 100 is capable of being used to assess a fall risk of a user and/or whether or not the user has potentially sustained a concussion.

While reference is made throughout this disclosure to, for example, "an illustrative embodiment", "one embodiment", or a "further embodiment", it is to be understood that some or all aspects of these various embodiments may be combined with one another as part of an overall embodiment of the invention. That is, any of the features or attributes of the aforedescribed embodiments may be used in combination with any of the other features and attributes of the aforedescribed embodiments as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A body sway measurement system, comprising:
an inertial measurement unit or camera configured to generate time series output data for determining one or more parameters indicative of the body sway of a user; and
a mobile device including a data processor, the data processor including at least one hardware component, the data processor being operatively coupled to the inertial measurement unit or camera, the data processor configured to receive the time series output data from the inertial measurement unit or camera, and the data processor and/or a cloud server configured to determine the one or more parameters indicative of the body sway of the user using a neural network;
wherein the data processor and/or the cloud server is configured to determine the one or more parameters indicative of the body sway of the user by performing the following steps:
collecting, during training of the neural network, a plurality of time series training datasets that correspond to respective ones of a plurality of different determinate classes, the plurality of time series training datasets comprising a time series raw inertial measurement unit output dataset, the plurality of different determinate classes corresponding to respective numerical values on a sway stability scale, the sway stability scale comprising a first end value, a second end value, and a plurality of intermediate values between the first end value and the second end value, the first end value on the sway stability scale being indicative of poor body stability, the second end value on the sway stability scale being indicative of excellent body stability, and the plurality of intermediate values being indicative of body stability classifications between poor and excellent body stability;
associating, during training of the neural network, each of the plurality of the time series training datasets with a particular one of the plurality of different determinate classes, wherein associating each of the plurality of the time series training datasets with a particular one of the plurality of different determinate classes includes pairing the time series raw inertial measurement unit output dataset with a particular one of the plurality of different determinate classes;
inputting, during inference, the time series output data from the inertial measurement unit or camera into the neural network that has previously undergone training; and
utilizing the trained neural network to associate the time series output data with one of the plurality of different determinate classes so as to generate the one or more parameters indicative of the body sway of the user.

2. The body sway measurement system according to claim 1, wherein the trained neural network is selected from the group consisting of: (i) a convolutional neural network (CNN), (ii) an inception network, (iii) an echo state network, and (iv) combinations thereof.

3. The body sway measurement system according to claim 1, wherein the mobile device is selected from the group consisting of: (i) a smartphone, (ii) a tablet computing device, (iii) a laptop computing device, (iv) a smartwatch, and (v) a head-mounted display.

4. The body sway measurement system according to claim 1, wherein the mobile device comprises the inertial measurement unit or the camera configured to generate the output data for determining the one or more parameters indicative of the body sway of the user; and
wherein the data processor of the mobile device and/or the cloud server is configured to determine the one or more parameters indicative of the body sway of the user based upon the output data from the inertial measurement unit or the camera.

5. The body sway measurement system according to claim 1, wherein the inertial measurement unit or the camera configured to generate the output data for determining the one or more parameters indicative of the body sway of the user is located remotely from the mobile device; and
wherein the data processor of the mobile device and/or the cloud server is configured to determine the one or more parameters indicative of the body sway of the user based upon the output data from the remotely located inertial measurement unit or camera.

6. The body sway measurement system according to claim 1, wherein the one or more parameters indicative of the body sway of the user determined by the data processor of the mobile device are selected from the group consisting of: (i) a sway stability score, (ii) a sway angle of the user, (iii) sway coordinates of the user, (iv) a sway envelope of the user, (v) a sway velocity of the user, and (vi) a sway area of the user.

7. The body sway measurement system according to claim 1, wherein the data processor of the mobile device and/or the cloud server is further configured to determine a fall risk of the user based upon the one or more parameters indicative of the body sway of the user.

8. The body sway measurement system according to claim 1, further comprising a visual display device including an output screen, the visual display device operatively coupled to the data processor, and the visual display device configured to display at least one manipulatable element of an interactive game on the output screen so that the at least one manipulatable element is visible to the user; and wherein the data processor is programmed to control the movement of the at least one manipulatable element of the interactive game displayed on the output screen of the visual display device by using the one or more parameters indicative of the body sway of the user, and the data processor is further programmed to determine a fall risk of the user based upon the performance of the user while playing the interactive game.

9. The body sway measurement system according to claim 1, further comprising a visual display device including an output screen, the visual display device operatively coupled to the data processor, and the visual display device configured to display a first object and a second object on the output screen so that the first and second objects are visible to the user; and wherein the data processor is programmed to displace the first object on the output screen of the visual display device, and the data processor is further programmed to control the movement of the second object on the output screen of the visual display device by using the one or more parameters indicative of the body sway of the user so that the user is able to attempt to follow the first object on the output screen with the second object by controlling the movement of the second object based upon his or her body sway.

10. The body sway measurement system according to claim 1, wherein the mobile device comprises the inertial measurement unit and the camera configured to generate the output data for determining the one or more parameters indicative of the body sway of the user; and wherein the data processor of the mobile device and/or the cloud server is configured to determine the one or more parameters indicative of the body sway of the user based upon the output data from both the inertial measurement unit and the camera.

11. A body sway measurement system, comprising:

an inertial measurement unit or camera configured to generate time series output data for determining one or more parameters indicative of the body sway of a user; and a computing device including a data processor, the data processor including at least one hardware component, the data processor being operatively coupled to the inertial measurement unit or camera, the data processor configured to receive the time series output data from the inertial measurement unit or camera, and the data processor and/or a cloud server configured to determine the one or more parameters indicative of the body sway of the user using a neural network;

wherein the data processor and/or the cloud server is configured to determine the one or more parameters indicative of the body sway of the user by performing the following steps:

collecting, during training of the neural network, a plurality of time series training datasets that correspond to respective ones of a plurality of different determinate classes, the plurality of time series training datasets comprising a time series raw inertial measurement unit output dataset, the plurality of different determinate classes corresponding to respective numerical values on a sway stability scale, the sway stability scale comprising a first end value, a second end value, and a plurality of intermediate values between the first end value and the second end value, the first end value on the sway stability scale being indicative of poor body stability, the second end value on the sway stability scale being indicative of excellent body stability, and the plurality of intermediate values being indicative of body stability classifications between poor and excellent body stability;

associating, during training of the neural network, each of the plurality of the time series training datasets with a particular one of the plurality of different determinate classes, wherein associating each of the plurality of the time series training datasets with a particular one of the plurality of different determinate classes includes pairing the time series raw inertial measurement unit output dataset, with a particular one of the plurality of different determinate classes;

inputting, during inference, the time series output data from the inertial measurement unit or camera into the neural network that has previously undergone training; and utilizing the trained neural network to associate the time series output data with one of the plurality of different determinate classes so as to generate the one or more parameters indicative of the body sway of the user.

12. The body sway measurement system according to claim 11, wherein the trained neural network is selected from the group consisting of: (i) a convolutional neural network (CNN), (ii) an inception network, (iii) an echo state network, and (iv) combinations thereof.

13. The body sway measurement system according to claim 11, wherein the computing device is selected from the group consisting of: (i) a desktop computing device, (ii) a tower computing device, (iii) a server computing device, (iv) a small-form-factor personal computer, (v) a smartphone, (vi) a tablet computing device, (vii) a laptop computing device, and (viii) a smartwatch.

14. The body sway measurement system according to claim 11, wherein the computing device comprises the inertial measurement unit or the camera configured to generate the output data for determining the one or more parameters indicative of the body sway of the user; and wherein the data processor of the computing device and/or the cloud server is configured to determine the one or more parameters indicative of the body sway of the user based upon the output data from the inertial measurement unit or the camera.

15. The body sway measurement system according to claim 11, wherein the inertial measurement unit or the camera configured to generate the output data for determining the one or more parameters indicative of the body sway of the user is located remotely from the computing device; and wherein the data processor of the computing device and/or the cloud server is configured to determine the one or more parameters indicative of the body sway of the user based upon the output data from the remotely located inertial measurement unit or camera.

16. The body sway measurement system according to claim 11, wherein the one or more parameters indicative of the body sway of the user determined by the data processor of the computing device are selected from the group consisting of: (i) a sway stability score, (ii) a sway angle of the user, (iii) sway coordinates of the user, (iv) a sway envelope of the user, (v) a sway velocity of the user, and (vi) a sway area of the user.

17. The body sway measurement system according to claim 11, wherein the data processor of the computing device and/or the cloud server is further configured to determine a fall risk of the user based upon the one or more parameters indicative of the body sway of the user.

18. The body sway measurement system according to claim 1, wherein, during training of the neural network, at least another one of the plurality of time series training datasets comprises a ground truth dataset collected using a force plate or balance plate, the ground truth dataset being collected using the force plate or balance plate while the time series raw inertial measurement unit output dataset, or a time series keypoint output dataset is being collected using the inertial measurement unit or the camera.

19. The body sway measurement system according to claim 1, wherein the data processor is configured to determine the one or more parameters indicative of the body sway of the user by using a convolutional neural network (CNN) to process the output data from the camera; and wherein, during training of the neural network, at least one of the plurality of time series training datasets comprises a time series keypoint output dataset, the time series keypoint output dataset comprising one or more keypoints for one or more locations on a body of the user.

20. The body sway measurement system according to claim 11, wherein, during training of the neural network, at least another one of the plurality of time series training datasets comprises a ground truth dataset collected using a force plate or balance plate, the ground truth dataset being collected using the force plate or balance plate while the time series raw inertial measurement unit output dataset, or a time series keypoint output dataset is being collected using the inertial measurement unit or the camera.

\* \* \* \* \*